United States Patent
Wennerberg et al.

(10) Patent No.: US 12,012,424 B2
(45) Date of Patent: Jun. 18, 2024

(54) PROCESS FOR PREPARATION OF BIS-CHOLINE TETRATHIOMOLYBDATE

(71) Applicant: ALEXION PHARMA INTERNATIONAL OPERATIONS UNLIMITED COMPANY, Dublin (IE)

(72) Inventors: Johan Anders Wennerberg, Lund (SE); Hans Roger Marcus Mårtensson, Malmo (SE)

(73) Assignee: Alexion Pharmaceuticals, Inc., Boston, MA (US)

( * ) Notice: Subject to any disclaimer, the term of this patent is extended or adjusted under 35 U.S.C. 154(b) by 897 days.

(21) Appl. No.: 16/970,379

(22) PCT Filed: Feb. 15, 2019

(86) PCT No.: PCT/EP2019/053871
§ 371 (c)(1),
(2) Date: Aug. 16, 2020

(87) PCT Pub. No.: WO2019/158719
PCT Pub. Date: Aug. 22, 2019

(65) Prior Publication Data
US 2020/0407385 A1    Dec. 31, 2020

Related U.S. Application Data (60) Provisional application No. 62/630,964, filed on Feb. 15, 2018.

(51) Int. Cl.
*C07F 11/00* (2006.01)
*C07C 213/08* (2006.01)

(52) U.S. Cl.
CPC .......... *C07F 11/005* (2013.01); *C07C 213/08* (2013.01)

(58) Field of Classification Search
CPC .............................. C07F 11/005; C07C 213/08
See application file for complete search history.

(56) References Cited

U.S. PATENT DOCUMENTS

2004/0019087 A1    1/2004   Ternansky et al.
2021/0094901 A1*   4/2021   Olsson ..................... A61K 9/28

FOREIGN PATENT DOCUMENTS

WO      2019154876 A1    8/2018

OTHER PUBLICATIONS

A Guidebook to Particle Size Analysis. Ed. Horiba Instruments Inc. 2017, 34 pages. (Year: 2017).*
Lee et al. "Reversible precipitation of bovine serum albumin by metal ions and synthesis, structure and reactivity of new tetrathiometallate chelating agents." J. Inorg. Biochem. 2007, 101, p. 1707-1718.
International Search Report and Written Opinion for International Application No. PCT/EP2019/053871, dated May 27, 2019.

* cited by examiner

*Primary Examiner* — Robert A Wax
*Assistant Examiner* — Olga V. Tcherkasskaya
(74) *Attorney, Agent, or Firm* — McDonnell Boehnen Hulbert & Berghoff LLP (57) ABSTRACT

A process is provided for the production of bis-choline tetrathiomolybdate, the process comprising reacting a choline salt with ammonium tetrathiomolybdate, wherein the choline salt is a hydroxide, acetate, or halide choline salt, wherein the process comprises: combining the choline salt with a first mixture of ammonium tetrathiomolybdate in water, wherein a molar excess of choline salt to ammonium tetrathiomolybdate is used, for a first reaction period to provide a first reaction mixture; subjecting the first reaction mixture to a reduced pressure for a second reaction period to provide a second reaction mixture; and, isolating bis-choline tetrathiomolybdate from the second reaction mixture, wherein isolating bis-choline tetrathiomolybdate comprises adding ethanol to the second reaction mixture.

20 Claims, 4 Drawing Sheets

PROCESS FOR PREPARATION OF BIS-CHOLINE TETRATHIOMOLYBDATE

CROSS-REFERENCE TO RELATED APPLICATIONS

This application is a national stage application under 35 U.S.C. § 371 of International Application No. PCT/EP2019/053871, filed Feb. 15, 2019, which claims priority from U.S. Provisional Patent Application No. 62/630,964, filed Feb. 15, 2018, the disclosures of each is incorporated by reference herein in their entirety.

FIELD OF THE DISCLOSURE

The present disclosure relates to an improved process for preparing bis-choline tetrathiomolybdate (BC-TTM).

BACKGROUND

Bis-choline tetrathiomolybdate can act as protein aggregator with an affinity for copper, and is thus considered potentially useful in the treatment of various diseases associated with aberrant vascularization, copper metabolism disorders, neurodegenerative disorders, obesity or NF-κB dysregulation. One area of interest is the use of bis-choline tetrathiomolybdate in the treatment of Wilson disease. Wilson disease is an autosomal recessive genetic disorder in which copper accumulates in tissues; this manifests as neurological or psychiatric symptoms and liver disease. It is treated by medication that reduces copper absorption or removes the excess copper from the body.

U.S. Patent Application Publication No. US 2004/0019087 (now U.S. Pat. No. 7,189,865, "the '865 Patent") discloses various thiomolybdate derivatives and their use in pharmaceutical compositions for the treatment or prevention of diseases associated with aberrant vascularization, copper metabolism disorders, neurodegenerative disorders, obesity or NF-κB dysregulation, and more particularly Wilson disease. A Phase II Study has been performed in Wilson disease patients with bis-choline tetrathiomolybdate (also referred to as bis[2-hydroxyethyl)trimethyl ammoniumitetrathiomolybdate, CAS No=649749-10-0). ClinicalTrials.gov NCT02273596.

Certain processes for preparing thiomolybdate derivatives are disclosed in the '865 Patent. The first process is illustrated in Scheme 1 below.

Scheme 1

In that process, addition of a quaternary ammonium hydroxide to thiomolybdate in the presence of water leads to cation exchange, providing the desired thiomolybdate derivative. The process is in equilibrium, and conversion to the product is disclosed as being driven by removal of volatile ammonia. It is disclosed that two equivalents of the quaternary ammonium hydroxide are added to one equivalent of ammonium tetrathiomolybdate in an aqueous solution, and that removal of ammonia is accomplished under reduced pressure with replacement of water as needed to maintain constant volume. The '865 Patent further discloses that the product was precipitated from solution by the addition of isopropanol, and then washed with isopropanol, ethanol and diethyl ether. In Examples 6.5, 6.24 and 6.25 of the '865 Patent, bis-choline tetrathiomolybdate was prepared from choline hydroxide and ammonium tetrathiomolybdate according to that method illustrated in Scheme 1 at scales ranging from 2 g to 140 g, with yields ranging from 65% to 83%.

The '865 Patent also discloses an alternative method for the synthesis of bis-choline tetrathiomolybdate in which two equivalents of choline hydroxide are added to one equivalent of ammonium molybdate in an aqueous solution, and then hydrogen sulfide gas ($H_2S$) is bubbled through the solution at room temperature (see '865 Patent, Examples 6.22 and 6.23). It is disclosed that, after purging the solution with nitrogen gas, the solvent (water) was removed repeatedly under reduced pressure to remove ammonia, and that the product needed to be redissolved in water and filtered to remove insoluble molybdenum sulfide. The '865 Patent disclosed that the product was recrystallized from water and isopropanol, and washed with ethanol and diethyl ether, to provide a 90% yield on a 1.5 g laboratory bench scale.

The necessity of large volumes of hydrogen sulfide gas, a poisonous, corrosive, flammable and explosive gas, renders this method inappropriate for large scale production of bis-choline tetrathiomolybdate. The method shown in Scheme 1 resulted only in relatively small-scale preparations of thiomolybdate derivatives with variable, often low, yield. Initial attempts to follow the method of Scheme 1 for the synthesis of bis-choline tetrathiomolybdate resulted in poor yields of 60% to 62%.

Thus, there remains a need for a process for the production of thiomolybdate derivatives, especially bis-choline tetrathiomolybdate, which process provides a high yield of thiomolybdate with a high level of purity at production scale or large scale.

SUMMARY OF THE DISCLOSURE

The present disclosure provides a process for the production of compound (I):

comprising reacting compound (II):

with compound (III):

(NH$_4$)$_2$MoS$_4$  (III)

wherein
X$^{-1}$ is OH$^{-1}$, acetate, or a halide;
wherein the process comprises:
combining compound (II) with a first mixture of compound (III) in water, wherein a molar excess of compound (II) to compound (III) is used, for a first reaction period to provide a first reaction mixture;
subjecting the first reaction mixture to a reduced pressure for a second reaction period to provide a second reaction mixture; and,
isolating compound (I) from the second reaction mixture, wherein isolating compound (I) comprises adding ethanol to the second reaction mixture.
compound (I) is bis-choline tetrathiomolybdate; compound (II) is a choline salt; and
compound (III) is ammonium tetrathiomolybdate.

The process of the disclosure provides the reaction product in good yield and with good purity in an economical reaction time without the need to use hydrogen disulphide.

In some embodiments, X$^{-1}$ is OH$^{-1}$.

In some embodiments, the process further comprises monitoring the evolution of ammonia during the step of subjecting the first reaction mixture to a reduced pressure.

In some embodiments, monitoring the evolution of ammonia comprises measuring the pH of vapour of a gas phase in contact with the first reaction mixture.

In some embodiments, achievement of pH of about 7 indicates that the second reaction period is complete.

In some embodiments, isolating compound (I) comprises adding from 2 to 4 volumes of ethanol to the second reaction mixture.

In some embodiments, the molar ratio of compound (II) to compound (III) is in the range of 4 to 20, 5 to 20, or 5 to 15.

In some embodiments, the total reaction time of the process is reduced by at least 50% compared to a process in which compound (II) is not used in a molar excess.

In some embodiments, compound (III) does not significantly decompose during the process.

In some embodiments, the first mixture of compound (III) in water is a slurry of compound (III) in water.

In some embodiments, the step of combining compound (II) with a first mixture of compound (II) in water is carried out at a temperature of 10° C. or less, preferably at a temperature of from 0° C. to 10° C.

In some embodiments, compound (II) is combined with the first mixture of compound (III) as an aqueous solution.

In some embodiments, the step of subjecting the first reaction mixture to a reduced pressure is carried out at a temperature of 35° C. or less, preferably at a temperature of from 5° C. to 35° C.

In some embodiments, the step of subjecting the first reaction mixture to a reduced pressure comprises subjecting the first reaction mixture to a pressure of 100 mbar or less, preferably to a pressure of from 0.1 mbar to 100 mbar.

In some embodiments, the step of isolating compound (I) from the second reaction mixture comprises precipitating compound (I) from the second reaction mixture and optionally filtering the second reaction mixture to obtain compound (I) as a solid.

In some embodiments, the process further comprises a recrystallization step, followed by optional polish filtering, optional washing with ethanol, drying of the resultant solid, and measurement of resulting particle size of the resultant solid.

In some embodiments, the resultant solid has a 50th percentile of particle size (D$_{50}$) of at least 30 μm, at least 40 μm, between 30 μm and 90 μm, or between 30 μm and 70 μm.

In some embodiments, the resultant solid has a 90th percentile of particle size (D$_{90}$) of between 60 μm and 550 μm, between 400 μm and 550 μm, between 75 μm and 135 μm, or between 75 μm and 100 μm.

In some embodiments, the resultant solid has a D$_{50}$ of less than 35 μm.

In some embodiments, the resultant solid has a D$_{90}$ of less than 75 μm.

In some embodiments, the resultant solid has a D$_{90}$-to-D$_{50}$ ratio less than 3.0, optionally less than or equal to 2.5 or optionally less than 2.0.

In some embodiments, at least one compound prepared according to any of the preceding claims and at least one pharmaceutically acceptable excipient.

The disclosure further provides a method of treating a patient with at least one disease associated with aberrant vascularization, copper metabolism disorders, neurodegenerative disorders, obesity, and NF-κB dysregulation, comprising administering a therapeutically effective amount of a compound prepared according to any of the preceding claims.

In some embodiments, the copper metabolism disorder is Wilson disease.

The disclosure further provides a kit for treating a patient with Wilson disease, the kit comprising a compound prepared according to any of the preceding claims, at least one pharmaceutically acceptable excipient, and instructions for administration to the patient.

These and other embodiments provided by the present disclosure are described in the Detailed Disclosure that follows.

DETAILED DESCRIPTION

The present disclosure provides an improved process for the large-scale synthesis of bis-choline tetrathiomolybdate, comprising treating an aqueous mixture of an ammonium thiomolybdate with an excess of a choline salt, exposing the resulting reaction mixture to a reduced pressure, and isolating the bis-choline tetrathiomolybdate from the resulting reaction mixture, the step of isolating the bis-choline tetrathiomolybdate comprising adding ethanol to the reaction mixture.

Preferably, the choline salt is choline hydroxide (i.e. the $X^{-1}$ counter-ion is $OH^{-1}$). In other words, preferably the choline salt is $[N(Me)_3(CH_2CH_2OH)][OH]$.

Definitions

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. Other features and advantages of the present disclosure will be apparent from the following description, Examples, and claims.

As used herein, the word "a," "an" or "plurality" before a noun represents one or more of the particular noun. For example, the phrase "a compound" represents "one or more compounds." Where the plural form (e.g. compounds, salts) is used, this includes the singular (e.g. a single compound, a single salt). "A compound" does not exclude that (e.g. in a pharmaceutical formulation) where more than one compound or salt is present.

As used herein, the term "about" is meant to account for variations due to experimental error. All measurements reported herein are understood to be modified by the term "about," whether or not the term is explicitly used, unless explicitly stated otherwise.

As used herein, the terms "for example" and "such as," and grammatical equivalences thereof, the phrase "and without limitation" is understood to follow unless explicitly stated otherwise.

As used herein, the term "isolating" refers to any means of separating a compound (e.g. a thiomolybdate derivative, especially bis-choline tetrathiomolybdate) from a solution comprising a solvent and, in some cases, impurities. Isolating may include precipitating the compound from the solution (e.g. with ethanol or an ethanol/water mixture) and/or filtering the resulting solid compound. Isolating may include one or more washing steps. Isolating removes at least about 50%, 60%, 70%, 80%, 82%, 85%, 87%, 90%, 92%, 95%, 96%, 97%, 98%, 99%, 99.5%, or 99.9% of the solvent and/or impurities in the solution.

As used herein, the terms "patient" and "patients" are understood to represent any subject (especially a mammal, especially a human) for administration of a compound according to the disclosure, unless explicitly stated otherwise.

As used herein, the term "precipitating" means to cause a compound (e.g. a thiomolybdate derivative, especially bis-choline tetrathiomolybdate) to separate from a solution into solid form. A compound may be precipitating from aqueous solution by, for example, adding ethanol or a water/ethanol mixture to the solution. In some cases, precipitating may cause one compound to separate from solution while a second compound (e.g. an impurity) remains in solution. Precipitating may cause at least about 50%, 60%, 70%, 80%, 82%, 85%, 87%, 90%, 92%, 95%, 96%, 97%, 98%, 99%, 99.5%, or 99.9% of the compound to separate from the solution as a solid (e.g. a crystalline solid).

As used herein, the term "significantly" refers to a change that is statistically significant, not due to chance alone, and observable using chemical or physical methods. For example, a compound (e.g., $(NH_4)_2MoS_4$) "does not significantly decompose" means that less than about 25%, 20%, 15%, 10%, 7%, 5%, 4%, 3%, 1%, or 0.5% w/w of the compound decomposes.

As used herein, the term "complete" with respect to a chemical reaction means that the chemical reaction has proceeded to completion, or nearly to completion. A chemical reaction is said to be complete when allowing additional time to elapse, without changing process parameters (such as temperature) or adding new reagents, will not cause a significant increase in the yield of the product of the chemical reaction. Complete may mean that the reaction is 85%, 87%, 90%, 92%, 95%, 96%, 97%, 98%, 99%, or 99.5% complete, i.e. that continuing the chemical reaction longer would cause at most a 15%, 13%, 10%, 8%, 5%, 4%, 3%, 2%, 1%, or 0.5% increase in the yield of the product of the chemical reaction.

As used herein, the term "yield" with respect to a chemical reaction refers to the amount of product obtained in a chemical reaction. The percentage yield (also termed fractional yield or relative yield) is calculated by dividing the amount of the desired product obtained by the theoretical yield. The theoretical yield is the amount of product that would be obtained if all reactants in the chemical reaction converted stoichiometrically to product with no remaining reactants and no reactant lost to side reactions. Yield may also be reported as absolute yield in grams (mass yield) or in moles (molar yield). With respect to a process involving multiple chemical reactions, yield refers to the amount of product obtained for the entire process. The percentage yield of a process is the amount of desired product obtained from the process divided by the amount of product that would be obtain if each chemical reaction in the process achieved the theoretical yield for that reaction step.

As used herein, "high yield" refers to a process with a percentage yield of at least 70%, 75%, 80%, 85%, 90%, or 95%.

As used herein, the term "large scale" refers to a chemical reaction, or process involving multiple chemical reactions, that yields at least one kilogram (kg) of a desired product. A large scale process may yield 1 kg, 2.5 kg, 5 kg, 7.5 kg, 10 kg, 12 kg, 15 kg, 20 kg, 25 kg or more of the desired product (e.g. a thiomolybdate derivative, especially bis-choline tetrathiomolybdate).

As used herein, the term "small scale" refers to a chemical reaction, or process involving multiple chemical reactions, that yields less than 100 grams (g) of a desired product. A small scale process may yield about 100 g, 50 g, 40 g, 30 g, 20 g, 10 g, or less of the desired product (e.g. a thiomolybdate derivative, especially bis-choline tetrathiomolybdate).

As used herein, "high level of purity" refers to a purity of at least about 95%. A compound having high level of purity may be at least about 80%, 82%, 85%, 87%, 90%, 92%, 95%, 96%, 97%, 98%, 99%, 99.5%, or 99.9% free of impurities. The level of purity as a percentage may be calculated by dividing the amount of the desired compound (e.g. a thiomolybdate derivative, especially bis-choline tetrathiomolybdate) by the total amount of the desired compound plus any impurities. When purity is assessed by high-performance liquid chromatography (HPLC), the amount of the compound or impurities is measured in terms of the integrated area under the curve above baseline of the chromatogram.

As used herein, the term "Dx(10)/μm" refers to the 10th percentile of particle size ($D_{10}$) measured in micrometers (μm). As used herein, the terms "Dx(50)/μm" or "median particle size" refer to the $50^{th}$ percentile particle size ($D_{50}$). As used herein, the term "Dx(90)/μm" refers to the 90th percentile of particle size ($D_{90}$).

As used herein, the terms "Wilson disease," "Wilson's disease," or "WD" are equivalent and represent an autosomal recessive genetic disorder in which copper accumulates in tissues of a patient.

Without wishing to be bound by theory, the present inventors believe that the reaction of the process of the disclosure proceeds according to the following equilibria when the choline salt is choline hydroxide:

[NH$_4$]$_2$[MoS$_4$]+2[N(Me)$_3$(CH$_2$CH$_2$OH)][OH]⇌[N(Me)$_3$(CH$_2$CH$_2$OH)]$_2$[MoS$_4$]+2NH$_3$+2H$_2$O

NH$_3$(g)⇌NH$_3$(l)

NH$_3$(l)+H$_2$O⇌[NH$_4$][OH]

The reduced pressure removes ammonia released during the reaction, and thus drives the reaction to completion following Le Chatelier's principle (the ammonium tetrathiomolybdate starting material and the bis-choline tetrathiomolybdate product being in equilibrium). Subjecting the reaction mixture to a reduced pressure is also believed to assist in reducing reaction time, thereby allowing the bis-choline tetrathiomolybdate product to be isolated more quickly. A shorter reaction time helps to avoid decomposition of the thiomolybdate species during the reaction. The process of the disclosure works very well and reliably affords the bis-choline tetrathiomolybdate product in both high yield and high purity.

The combination step comprises combining a molar excess of compound (II) with compound (III), i.e. a molar ratio of compound (II) to compound (III) of Z:1, wherein Z is greater than 2 (i.e. more than two parts of compound (II) for each one part of compound (III), is used. Without wishing to be bound by theory, the present inventors believe that the use of an excess of choline salt assists in favouring the product side of the reaction equilibrium. Using an excess of choline salt is also believed to assist in reducing reaction time, thereby allowing the bis-choline tetrathiomolybdate product to be isolated more quickly and helping to avoid decomposition of the thiomolybdate species. When the molar ratio of compound (II) to compound (III) of 2:1 (i.e. Z is 2) was used in a small-scale preparation of bis-choline tetrathiomolybdate in methanol, the present inventors found that the vapour released during the reaction had a stable pH of 7 after 3 hours. That small scale reaction was repeated in methanol with a molar ratio of 10:1 (i.e. Z is 10) and the pH of the vapour measured as shown in Table 1.

TABLE 1

| Time (min) | pH |
| --- | --- |
| 25 | 10 |
| 45 | 8-9 |
| 60 | 7-8 |
| 80 | 7 |

The present inventors found that when the small-scale preparation of bis-choline tetrathiomolybdate was carried out in methanol with a molar ratio of choline hydroxide to ammonium tetrathiomolybdate of 10:1, the time taken for complete release of ammonia was significantly reduced, from 180 minutes to 80 minutes.

Optionally, the molar ratio of compound (II) to compound (III) is Z:1, wherein Z is 3 or greater, or 4 or greater, or 5 or greater, or 6 or greater, for example 7 or greater. Preferably, Z is up to 20, especially up to 15, for example up to 12. For example, Z may be in the range of from above 2 to 20, for example in the range of 3, or 4, or 5, or 6, to 20, for example 8, or 10, or 12 to 20, for example 3, or 4, or 5, or 6, or 8, or 10 or 12 to 15, for example 12 to 15. Especially, Z is in the range of from 5 to 20, preferably from 5 to 15, especially from 5 to 12, for example from 5 to 7. Optionally, and especially when Z is in the range of from 5 to 20, the total reaction time of the process is reduced by at least 50% compared to a process in which Z is 2 or less. Additionally or alternatively, especially when Z is in the range of from 5 to 20, the time taken for the second reaction period to be complete is reduced by at least 50% compared to a process in which Z is 2 or less. When the process comprises measuring the pH of vapour of a gas phase in contact with the first reaction mixture, it may be that the second reaction period is deemed to be complete when the measured pH is about 7.

Preferably, compound (III) does not significantly decompose during the process. It will be understood that the expected reaction of compound (III) with compound (II) to form compound (I) is not decomposition of compound (III). For example, it may be that decomposition of compound (III) is thermal decomposition, such as thermal decomposition into unwanted side products. It will be understood that 'unwanted side products' may be molybdenum species other than compound (I) or compound (III).

The step of isolating compound (I) from the second reaction mixture comprises adding ethanol to the second reaction mixture. The present inventors have surprisingly found that adding ethanol to the second reaction mixture aids the isolation of compound (I) in a relatively pure form. For example, it may be that adding ethanol to the second reaction mixture causes the precipitation of compound (I) while leaving compound (II) in solution. It will be appreciated separating compound (I) from a reaction mixture comprising compound (I) and compound (II) may be particularly useful when an excess of compound (II) is used in the preparation of compound (I). The present inventors have surprisingly found that choline hydroxide has good solubility in ethanol-water mixtures, while bis-choline tetrathiomolybdate has poor solubility in ethanol-water mixtures, and that the use of ethanol in the isolating step provides bis-choline tetrathiomolybdate in high yield with a high purity. More particularly, the use of ethanol instead of isopropanol to precipitate bis-choline tetrathiomolybdate is advantageous. This is surprising because if bis-choline tetrathiomolybdate is recrystallized from an alcohol, the degree of purification is comparable whether ethanol or isopropanol is used. However, if isopropanol is used instead of ethanol in the isolating step of the present disclosure, precipitation of excess choline hydroxide occurs, leading to a relatively impure product compared with the product obtained using ethanol.

Preferably, the isolating step comprises treating the second mixture with 2 to 4 volumes, for example about 3 volumes, of ethanol to precipitate compound (I). The present inventors have found that the use of 3 volumes of ethanol gave a good yield in the preparation of bis-choline tetrathiomolybdate.

Depending on the conditions employed, the compound (I) can be isolated as a solvate, for example a hydrate.

The process of the disclosure is effective for the production of compounds disclosed in the '865 Patent (US 2004/0019087).

Reference will now be made in detail to specific embodiments. While the disclosure will be described in conjunction with these specific embodiments, it will be understood that it is not intended to limit the invention to those embodiments.

Optionally, the step of combining compound (II) with a first mixture of compound (III) in water is carried out at a temperature of 40° C. or less, such as 35° C. or less, for example at room temperature or less. Preferably, the step of combining compound (II) with a first mixture of compound (III) in water is carried out at a temperature of 10° C. or less, such as 8° C. or less, for example 5° C. or less. Preferably, the step of combining compound (II) with a first mixture of compound (III) in water is carried out at a temperature of from 0° C. to 10° C., for example 0° C. to 5° C. Preferably, the first reaction period is a period of 90 minutes or less, for example one hour or less. Preferably the compound (II) is added to the first mixture of compound (III) in water.

Preferably, the step of subjecting the first reaction mixture to a reduced pressure is carried out at a temperature of 37° C. or less, for example 35° C. or less, such as 33° C. or less, for example 30° C. or less. Preferably, the step of subjecting the first reaction mixture to a reduced pressure is carried out at a temperature of from 5° C. to 35° C., for example 10° C. to 33° C., for example 25° C. to 30° C., or alternatively 10° C. to 20° C. Preferably, the second reaction period is a period of from 30 minutes to 10 hours, from 1 to 8 hours, for example 2 to 6 hours.

It is postulated low temperatures preferably employed in the process reduce the decomposition of the thiomolybdate species. That has been achieved by the method of the disclosure whilst maintaining the overall rate of the formation of product at a practical and economic level.

Preferably, the first mixture of compound (III) in water is a slurry of compound (III) in water. The present inventors have found that it is not necessary for compound (III) to be fully dissolved in water during the addition step. The use of a slurry enables the volume of water to be smaller than would be needed for a solution, and the smaller volume of water assists in control of the temperature. It has been found that use of compound (III) in a slurry does not have any detrimental effects on the rate of reaction, the yield, or the purity of the product.

Preferably, compound (II) is added to the first mixture of compound (III) as a solution. The solution may be substantially free, or free, from methanol, for example it may be an aqueous solution. The present inventors have found that the step of isolating compound (I) from the second reaction mixture can be carried out more easily, and that the process affords a higher yield, when compound (II) is added as a solution substantially free from methanol. Without wishing to be bound by theory, the present inventors believe that the presence of methanol can prevent precipitation of compound (I) from the second reaction mixture during the isolating step. Preferably, an aqueous solution of compound (II) is added dropwise to the aqueous mixture of compound (III). Dropwise addition facilitates control of the temperature of the resulting reaction mixture.

It will be appreciated that a reduced pressure is a pressure lower than atmospheric pressure. Preferably, the step of subjecting the first reaction mixture to a reduced pressure comprises subjecting the first reaction mixture to a pressure of 100 mbar or less, such as 50 mbar or less, for example 25 mbar or less. Preferably, the step of subjecting the first reaction mixture to a reduced pressure comprises subjecting the first reaction mixture to a pressure of from 0.1 mbar to 100 mbar, such as from 0.5 mbar to 50 mbar, for example from 1 mbar to 25 mbar.

Without wishing to be bound by theory, the present inventors believe that, since ammonia is formed during the reaction, the reaction of compound (III) with compound (II) can be monitored by following the formation of ammonia. The present inventors found that the pH of the vapour formed during the reaction can be estimated by applying a stream of nitrogen gas over the surface of the reaction mixture and testing the $N_2$ stream using moist pH indicator sticks. In a test reaction, a pH of 10 was measured in the vapour 5 minutes after the reaction started. The first reaction mixture was left to stir overnight at 30° C., after which time the vapour was found to have a pH of 7, indicating that no more ammonia was being released.

Preferably, the process comprises monitoring the evolution of ammonia during the step of subjecting the first reaction mixture to a reduced pressure. It may be that monitoring the evolution of ammonia during the step of subjecting the first reaction mixture to a reduced pressure provides an indication on the progress of the reaction, for example allowing the step of isolating compound (III) from the second reaction mixture to be commenced as soon as the reaction is complete. It will be appreciated that it is generally desirable to minimise the period during which a reaction product is maintained in solution. Preferably, the step of monitoring the evolution of ammonia comprises detecting the presence of ammonia in the gas phase, for example at intervals, during the step of subjecting the first reaction mixture to a reduced pressure. Optionally, the step of monitoring the evolution of ammonia comprises determining the basicity of the gas phase, for example by measuring the pH of the gas phase. Preferably, the process comprises subjecting the first reaction mixture to a reduced pressure until substantially no ammonia is detected in the gas phase. Preferably, the process comprises subjecting the first reaction mixture to a reduced pressure until the pH of the gas phase is found to be essentially neutral, such as having a pH of from 6 to 8, for example a pH of about 7. The exact time necessary depends on the concentration of the reagents and the temperature of the reaction mixture. For example, the second reaction period is a period of from 30 minutes to 10 hours, from 1 to 8 hours, for example 2 to 6 hours. Optionally, when the process comprises monitoring the evolution of ammonia during the step of subjecting the first reaction mixture to a reduced pressure, achievement and/or detection of a pH of about 7 indicates that the second reaction period is complete.

Preferably, the step of isolating compound (I) from the second reaction mixture comprises precipitating compound (I) from the second reaction mixture. Additionally or alternatively, the step of isolating compound (I) from the second reaction mixture may comprise filtering the second reaction mixture to obtain compound (I) as a solid.

Compound (I) can be further recrystallized, for example as described in PCT/EP2019/052940. In certain embodiments of the invention, Compound (I) can be recrystallized by (a) providing a solution Compound (I); (b) heating the solution of Compound (I) to a first temperature between about 35° C. and 50° C.; (b) gradually adding ethanol or isopropanol to the solution of Compound (I) over a time period of at least one hour; (c) cooling the solution of Compound (I) to a second temperature between about 10° C.

and 25° C. to produce solid Compound (I); (d) filtering the solid Compound (I); (e) drying the solid Compound (I) at a third temperature between about 20° C. and 30° C. under reduced pressure.

In particular embodiments of the invention, the crystalline particles of Compound (I) have a $50^{th}$ percentile of particle size ($D_{50}$) of at least 30 μm. In other embodiments, the crystalline particles have a $D_{50}$ of at least 40 μm. In other embodiments, the crystalline particles have a $D_{50}$ of between 30 μm and 90 μm. In other embodiments, the crystalline particles have a $D_{50}$ of between 30 μm and 70 μm.

In particular embodiments of the invention, the crystalline particles of Compound (I) have a $50^{th}$ percentile of particle size ($D_{50}$) of at least 30 μm, or at least 40 μm, or between 30 μm and 70 μm, and a 90th percentile of particle size ($D_{90}$) of between 75 μm and 550 μm. In other embodiments, the $D_{90}$ is between 400 μm and 550 μm. In other embodiments, the $D_{90}$ is between 75 μm and 135 μm. In other embodiments, the $D_{90}$ is between 75 μm and 100 μm.

In an embodiment, the crystalline particles have a $D_{90}$-to-$D_{50}$ ratio of less than 2.5. In an embodiment, the $D_{50}$ is less than 35 μm. In an embodiment, the $D_{90}$ is less than 75 μm. In an embodiment of the disclosed compositions, the crystalline particles have a 10th percentile of particle size ($D_{10}$) of less than 15 μm.

Compounds (II) and (III) are known, and are available commercially, or can be made by known methods.

Figure 3:
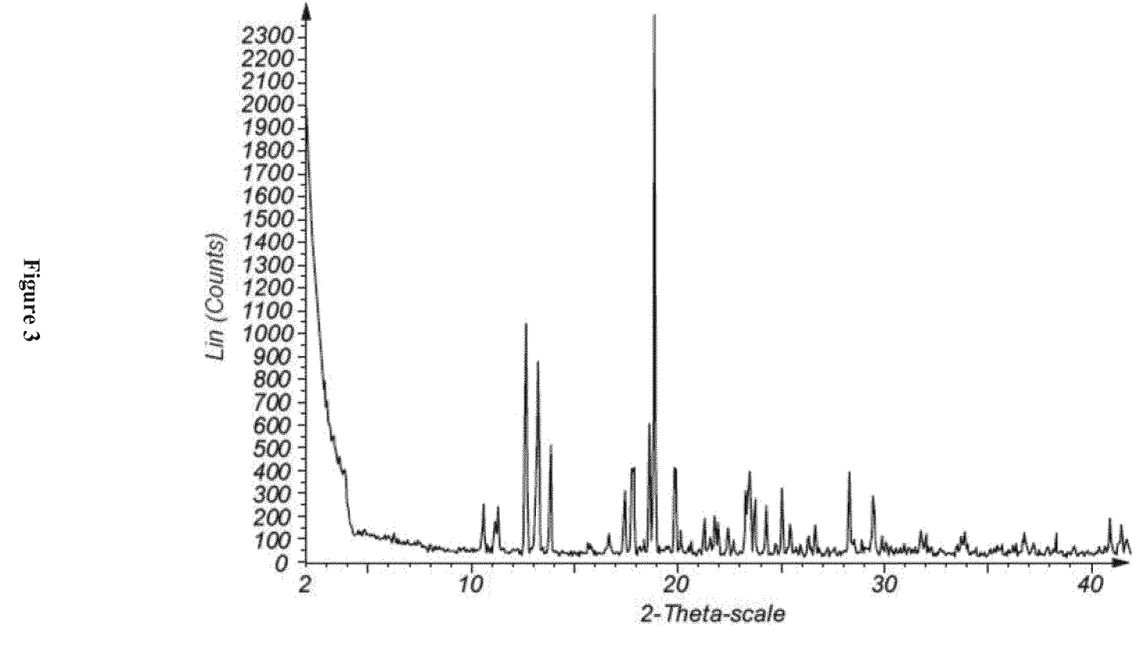
FIG. 3 shows a X-Ray Powder Diffraction (XRPD) pattern of bischoline tetrathiomolybdate Form 1, carried out on a PANalytical X'Pert PRO instrument, equipped with a Cu, long fine focus X-ray tube and a PIXcel detector. The x-axis shows 2-theta positions as obtained with CuK-alpha1 radiation.
Figure 4:
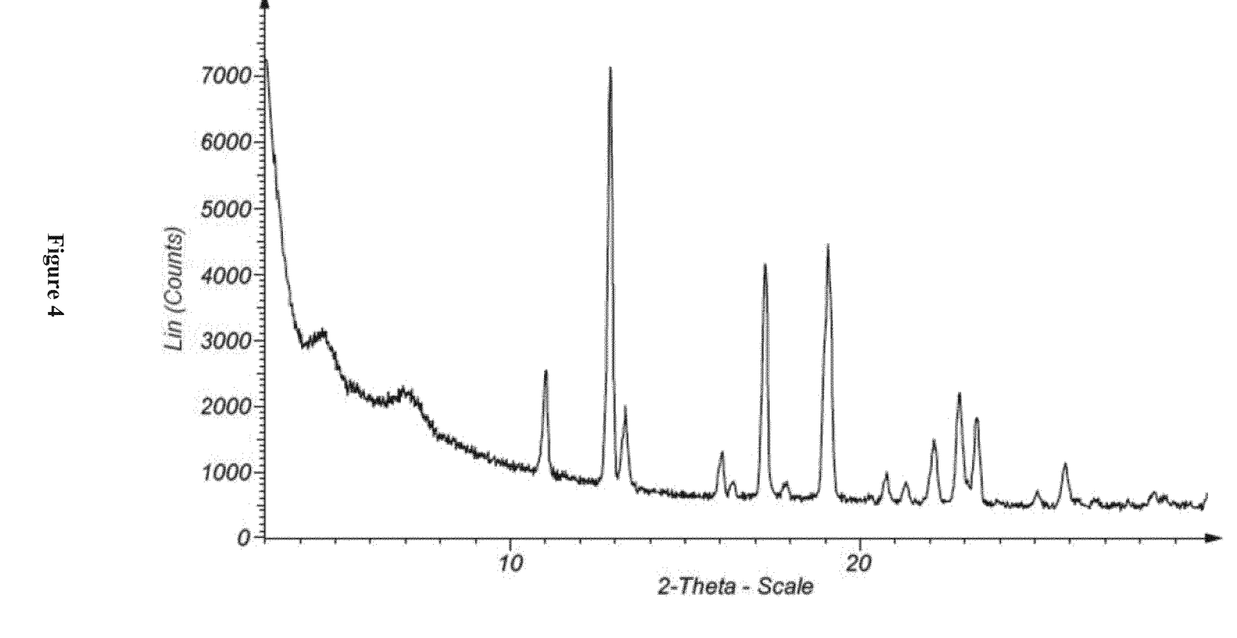
FIG. 4 shows a XRPD pattern of bischoline tetrathiomolybdate Form 2, carried out on a PANalytical X'Pert PRO instrument, equipped with a Cu, long fine focus X-ray tube and a PIXcel detector. The x-axis shows 2-theta positions as obtained with CuK-alpha1 radiation.

Bis-choline tetrathiomolybdate, compound (I), can exist in a number of different crystal forms. One crystal form, referred to as Form 1, has an X-ray powder diffraction pattern, as obtained with CuKα1-radiation, with characteristic peaks at diffraction angles (° 2theta) of 12.64±0.15 and 18.89±0.15; more specifically with characteristic peaks at diffraction angles (° 2theta) of 12.64±0.15; 13.84±0.15; 18.64±0.15; 18.89±0.15; and 19.86±0.15; and more specifically having an X-ray powder diffraction pattern essentially as set out in Table 3 in Example 4, or essentially as set out in FIG. 3.

Figure 2:
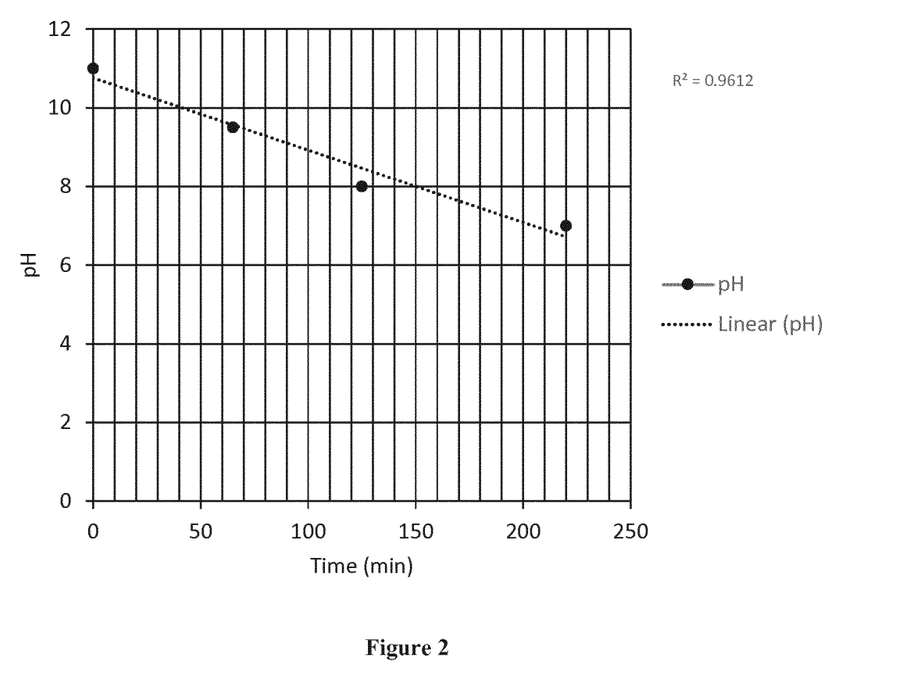
FIG. 2 is a graph showing the relationship between pH of the reaction mixture against time for a process as disclosed herein.

Another crystal form, referred to as Form 2, has a X-ray powder diffraction pattern, as obtained with CuKα1-radiation, with characteristic peaks at diffraction angles (° 2theta) of 12.84±0.15 and 19.08±0.15; more specifically with characteristic peaks at diffraction angles (° 2theta) of 11.00±0.15; 12.84±0.15; 16.02±0.15; 17.28±0.15; and 19.08±0.15; and more specifically having an X-ray powder diffraction pattern essentially as set out in Table 4 in Example 5, or essentially as set out in FIG. 2.

Form 1 may be prepared by a method comprising:

a) adding ethanol to an aqueous solution of bis-choline tetrathiomolybdate of any crystal form, and keeping the solution at a temperature of from about 10 to about 40° C.;

b) stirring the solution at said temperature for at least about 5 minutes;

c) isolating the bis-choline tetrathiomolybdate Form 1 by filtration, followed by washing the bis-choline tetrathiomolybdate Form 1 with alcohol; and d) drying the bis-choline tetrathiomolybdate Form 1.

The solution in step a) is preferably kept at a temperature of from about 10 to about 35° C., or from about 10° C. to about 25° C. An alcohol other than ethanol could be used in step a) above.

The solution in step b) is preferably stirred for about 15 minutes to about 24 hours, for example for about 15 minutes to about 2 hours, for example for about 15 minutes to about 45 minutes.

The alcohol in step c) is preferably ethanol.

Alternative methods of preparing bis-choline tetrathiomolybdate Form 1 include:

Alternative A keeping a suspension of any crystal form of bis-choline tetrathiomolybdate at about 5° C. for about 3 days in a solvent or solvent combination selected from at least one of ethyl acetate, heptane, cumene, anisole, butyl acetate, isopropyl acetate, propyl acetate, methyl isobutylketone, methyl ethylketone, isopropyl alcohol, hexane, cyclohexane, 1,4-dioxolane, toluene, tetralin, chlorobenzene, tetrahydrofuran, dichloromethane, acetonitrile, dimethylamine, cyclohexanone, diisopropyl ether, tetrahydrofuran+about 5% $H_2O$, isopropylalcohol+about 5% $H_2O$, acetone+about 5% $H_2O$, 1,2,3,4-tetrahydronaftalen, morpholine, mesitylene, ethyl formate, tetradecafluorohexane, acetophenone, o-xylene, trimethylamine, ethylenediamine, and pyridine;

filtering the suspension and isolating a solid of crystalline material of bis-choline tetrathiomolybdate Form 1.

In this alternative, the solvent in one specific example is ethyl acetate.

Alternative B keeping a suspension of any crystal form of bis-choline tetrathiomolybdate at about 5-25° C. (about 4 hour cycles) for about 3 days in a solvent or solvent combination selected from at least one of ethyl acetate, heptane, cumene, anisole, butyl acetate, isopropyl acetate, propyl acetate, methyl isobutylketone, methyl ethylketone, isopropyl alcohol, hexane, cyclohexane, 1,4-dioxolane, toluene, tetralin, chlorobenzene, tetrahydrofuran, dichloromethane, acetonitrile, dimethylamine, cyclohexanone, diisopropyl ether, tetrahydrofuran+about 5% $H_2O$, isopropylalcohol+about 5% $H_2O$, acetone+about 5% $H_2O$, 1,2,3,4-tetrahydronaftalen, morpholine, mesitylene, ethyl formate, tetradecafluorohexane, acetophenone, o-xylene, trimethylamine, ethylenediamine, and pyridine; and filtering the suspension and isolating a solid of crystalline material of bis-choline tetrathiomolybdate Form 1.

In this alternative, the solvent in one specific example is ethyl acetate.

Alternative C keeping a suspension of any crystal form of bis-choline tetrathiomolybdate at about 37° C. in ethyl acetate;

filtering the suspension and isolating a solid of crystalline material of bis-choline tetrathiomolybdate Form 1.

Alternative solvents or solvent combinations to ethyl acetate include, but are not limited to, at least one selected from heptane, cumene, anisole, butyl acetate, isopropyl acetate, propyl acetate, methyl isobutylketone, methyl ethylketone, isopropyl alcohol, hexane, cyclohexane, 1,4-dioxolane, toluene, tetralin, chlorobenzene, tetrahydrofuran, dichloromethane, acetonitrile, dimethylamine, cyclohexanone, diisopropyl ether, tetrahydrofuran+5% $H_2O$, isopropylalcohol+5% $H_2O$, acetone+5% $H_2O$, 1,2,3,4-tetrahydronaftalen, morpholine, mesitylene, ethyl formate, tetradecafluorohexane, acetophenone, o-xylene, trimethylamine, ethylenediamine and pyridine.

Form 2 may for example be prepared by a method comprising:
a) heating bis-choline tetrathiomolybdate Form 1 from about 25° C. to about 80° C. at a temperature increase of about 10° C. per minute and;
b) isolating bis-choline tetrathiomolybdate Form 2 in the temperature range of about 55° C. to 57° C.

The isolation of material in step b) is carried out at 56.8° C.

Bis-choline tetrathiomolybdate Form 1 and Form 2 are both crystalline, non-solvated, forms.

For the avoidance of doubt, an embodiment or preferred aspect of any one feature of the method of the disclosure, or compound described herein, may be combined with any embodiment or preferred aspect of another feature of the method of the disclosure, or compound described herein, to create a further embodiment.

EXAMPLES

General Experimental Details

Figure 1:
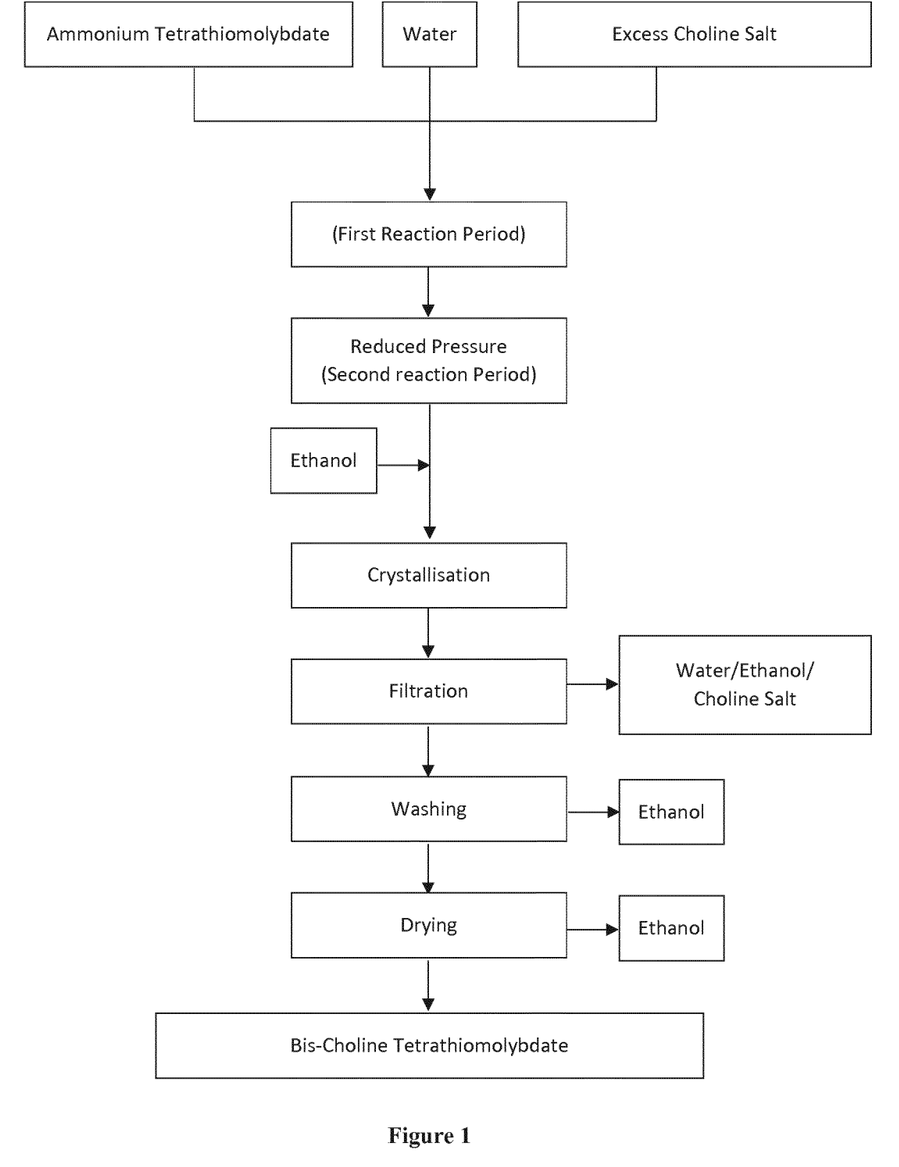
FIG. 1 is a general reaction scheme in accordance with the disclosure in a flow chart.

Unless stated otherwise, all reagents/solvents were purchased from commercial sources and used without further purification. The general reaction scheme is shown in the flow chart illustrated in FIG. 1.

Example 1—Preparation of Bis-Choline Tetrathiomolybdate—140 g Scale

The following equipment was used for the manufacture of bis-choline tetrathiomolybdate at 140 g scale:

Reaction: 4 L 3-necked, round bottomed flask, digital thermometer, mechanical stirrer (anchor style), septum, addition funnel (500 mL), condenser (water trap), gas trap (2 traps serially connected, −78° C.), vacuum pump (membrane pump, vacuum capacity on sealed empty system=5 mbar), pH indicator paper.

Precipitation: 5 L 3-necked, round bottomed flask, digital thermometer, mechanical stirrer (anchor style), addition funnel (500 mL).

A slurry of ammonium tetrathiomolybdate (100.0 g, 0.26 mol) in purified water (600 mL, 6 L/kg ammonium tetrathiomolybdate) was cooled to 3° C. with agitation at a speed of 280 rpm. Choline hydroxide (46 wt % in water, 600 mL; 276 g choline hydroxide, 2.28 mol) was added to the agitated slurry over 20 minutes with the temperature maintained at <5° C.

The resulting slurry mixture was then heated to 30° C. and the reaction vessel was subjected to a reduced pressure. Evolution of $NH_3$ was monitored by applying a stream of $N_2$ over the surface of the slurry and testing the vapour from the reaction vessel with moist pH indicator sticks. The slurry mixture was stirred under reduced pressure at 30° C. until no further evolution of $NH_3$ was detected. Temperature, pressure and pH were logged throughout the reaction and are listed in Table 2 below.

After 3.5 hours, the reaction solution was transferred to a 5 L 3-necked round bottomed flask through a sintered glass-funnel (Por. 3). No residues were found on the sintered glass funnel, indicating that no insoluble degradation by-products were formed during the reaction. The solution was cooled to 18° C., and then treated with ethanol (3600 mL) over 80 minutes while agitating the solution at a speed of 400-450 rpm and maintaining the temperature at 20° C. The resulting red slurry was stirred for 30 minutes and then the product collected on a sintered glass funnel. The product was washed with ice-cold ethanol (2×120 mL) and dried overnight under vacuum (approximately 25 mbar) at 25° C. to give 140.7 g (85% yield) of a red crystalline powder. The product had a purity of 99.7% as assessed by HPLC.

TABLE 2

| Time (min) | T (° C.) | P (mbar) | pH (gas phase) |
|---|---|---|---|
| 0 | 29.6 | | 11 |
| 5 | 29.3 | 34 | |
| 10 | 27.0 | 24 | |
| 30 | 27.2 | 16 | |
| 45 | 26.1 | 8 | |
| 65 | | | 9-10 |
| 80 | 28.5 | 4 | |
| 125 | | | 8 |
| 155 | 18.5 | 5 | |
| 170 | 22.0 | 5 | |
| 200 | 27.4 | 5 | |
| 220 | 32.1 | | 7 |

As shown in the graph of FIG. 2, a fairly linear relationship (R=0.96) was noted when plotting pH against time. The pH data recorded thus provided an approximate prediction of reaction time. A small temperature increase (3-5° C.) was noted when the reaction vessel was pressurized for testing pH, however the observed maximum temperature during the production was no more than 36° C., and those small and temporary increases in temperature did not appear to be detrimental to the quality of the product. The operational pressure for the empty reaction vessel was measured to 5 mbar, which was achieved by using a membrane pump. During the experiment, a build-up of ice in the gas traps was observed, leading to clogging of the vacuum line (which took around 30 minutes to resolve). The true reaction time is therefore believed to be shorter than observed.

Example 2— Preparation of Bis-Choline Tetrathiomolybdate—3.7 kg Scale

Ammonium tetrathiomolybdate (2.8 kg, 10.8 mol) and water (16.8 Kg) were added to a Hastelloy reactor. The resulting dark slurry was cooled to <5° C. and then choline hydroxide (18 kg, 148.5 mol) was added over 50 minutes at such a rate that the temperature did not exceed 5° C. Following addition of choline hydroxide, the mixture was heated to 30° C.

The reactor was placed under reduced pressure and the evolution of $NH_3$ monitored by measurement of pH in the gas phase with moist pH indicator paper. When no further evolution of $NH_3$ was observed (3 hours), 5 L of water was added to the reaction mixture to compensate for loss of water by evaporation and the reaction mixture was transferred to a stainless steel reactor via a cartridge filter. No residues were found on the filter, indicating that no insoluble degradation by-products were formed during the reaction. The filtered solution was cooled to 20° C. and then slowly treated with ethanol (80 Kg) over 25 minutes causing crystallisation of the BC-TTM product. Once the addition of ethanol was complete, the resulting slurry was stirred for 30 minutes.

The final product was then collected on a Hastelloy filter, washed twice with ethanol (2×4 Kg) and finally dried at 25° C. under vacuum and sieved with a 1.4 mm sieve to afford 3.7 kg of a red crystalline material, 78% yield. The BC-TTM product had a purity of 99.2% as assessed by HPLC.

Example 3—Preparation of Bis-Choline Tetrathiomolybdate—12 kg Scale

Ammonium tetrathiomolybdate (9.0 kg, 34.6 mol) and water (54 Kg) were added to a Hastelloy reactor. The resulting dark slurry was cooled to <5° C. and then choline hydroxide (55.0 kg, 454.5 mol) was added at such a rate that the temperature did not exceed 5° C. The addition took 90 minutes. Following addition of choline hydroxide, the mixture was heated to 30° C.

The reactor was placed under reduced pressure and the evolution of $NH_3$ monitored by measurement of pH in the gas phase with moist pH indicator paper. When no further evolution of $NH_3$ was observed (after around 5.5 hours), 16 L of water was added to the reaction mixture to compensate for loss of water by evaporation and the reaction mixture was transferred to a stainless steel reactor via a cartridge filter. No residues were found on the filter, indicating that no insoluble degradation by-products were formed during the reaction. The filtered solution was cooled to 20° C. and then slowly treated with ethanol (240 Kg) over 35 minutes causing crystallisation of the product. Once the addition of ethanol was complete, the resulting slurry was stirred for 60 minutes.

The final product was then collected on a Hastelloy filter, washed twice with ethanol (2×10 Kg) and finally dried at 25° C. under vacuum and sieved with a 1.4 mm sieve to afford 11.93 kg of a red crystalline material, 80% yield. The product had a purity of 99.5% as assessed by HPLC.

Example 4—Preparation of Bis-Choline Tetrathiomolybdate—12 kg Scale

Ammonium tetrathiomolybdate (9 kg) and water (54 L) were mixed under stirring to form a dark slurry in a corrosion-resistant jacketed and temperature controlled reactor (Hastelloy), previously purged with $N_2$ gas and maintained under low $N_2$ stream. The mixture was cooled to 15±5° C. with cold water.

Choline hydroxide (55.0 kg, 46% aqueous solution) in solution was added via a charging vessel, and the resulting solution was then heated to 30±3° C. with hot water. The reactor was then placed under reduced pressure to purge/degas formed ammonia via a tap water-containing scrubber. The reaction is continued until pH≤7.5 is reached, as determined by measuring the pH of the gas phase by use of moistened pH sticks (IPC). pH testing began 4 hours after the start of reaction, with hourly testing thereafter until pH≤7.5 was attained. Upon completion of reaction, the reaction mixture is transferred to a second, stainless steel reactor via cartridge filters. The amount of water lost from the reaction mixture is measured, and the water is replaced in the reactor (compensated). The solution is heated to 45±3° C. and ethanol is charged into the second reactor for 30-60 minutes. The mixture is then slowly cooled to 15±5° C. and stirred overnight.

The BC-TTM product is isolated on an oyster filter and is then washed twice with ethanol before being recharged to the second reactor for recrystallization. The compound in the second reactor is then dissolved in water and transferred to a glass-lined reactor via cartridge filters (0.45 μm and 0.2 μm). The solution in the glass-lined reactor was heated to 45±3° C., and then ethanol (undenatured, 95.5%, 304L) was charged over 30±10 minutes. The slurry was cooled slowly during at least 60 minutes to 15±° C.

After stirring the resulting slurry for at least 8 hours, the crystalline product was isolated on a cleaned oyster filter purged with $N_2$. The solid was washed twice with ethanol, and the oyster filter solid cake was blown dry for 30-60 minutes with $N_2$. Drying was performed under reduced pressure at 25±3° C. for at least 8 hours and/or until achieving constant weight. The product was then (optionally) sieved and packed. The product is stored in the freezer.

Some portion was dissolved in water until complete dissolution was achieved, stirring for 10±5 minutes after adding each additional water portion until full dissolution is achieved. The solution is filtered (via cartridge filter) and transferred to a jacketed reactor. Sufficient ethanol is charged over at least 2.5 hours to reach and ethanol/water ratio of 80/20 (w/w), and then cooled slowly over at least 60 minutes to 15±5° C., and then stirred for at least 8 hours at this temperature. The filtration and drying (at least 18 hours under reduced pressure at 25±3° C.) steps are then repeated; crystalline BC-TTM is then sieved (Quadro CoMil), packed, and stored in the freezer.

The resulting crystalline material is a red-orange to dark red or dark burgundy powder with a homogenous appearance. QC results in:

particle size measurement of $D_{50}$ between 30 μm and 70 μm and $D_{90}$ is between 75 μm and 100 μm;
insoluble impurities of <0.5% (w/w) by gravimetric test;
BC-TTM of 93-102% by HPLC; and the following impurity profile:

| Analyses | Limits | |
| --- | --- | --- |
| Bis-choline molybdate (HPLC) | Bischoline molybdate | ≤0.5% w/w |
| | Unknown impurity, RRT 0.7 | ≤0.1% w/w |
| Impurities (HPLC) | Bischoline thiomolybdate | ≤0.3% w/w |
| | Bischoline dithiomolybdate | ≤0.5% w/w |
| | Bischoline trithiomolybdate | ≤3.0% w/w |
| | Dimer S6 | ≤0.15% w/w |
| | Any other impurity | ≤0.15% w/w |
| | Total amount of impurities | ≤5.0% w/w |

Example 5. Bis-Choline Tetrathiomolybdate Form 1

A solution of bis-choline tetrathiomolybdate in water was cooled to approximately 20° C. Ethanol (3 vol/vol water) was slowly added to avoid a temperature increase and crystallization of bis-choline tetrathiomolybdate was initiated upon the ethanol addition. After completion of the ethanol charge, the solution was stirred for not less than 30 minutes. The crude drug substance was isolated by filtration and washed twice with cool ethanol. The drug substance was dried at 25° C. under vacuum.

X-Ray Powder Diffraction (XRPD) Analysis

X-Ray Powder Diffraction patterns were collected on a Bruker D8 diffractometer (Bruker AXS D8 Advance) using Cu Kα radiation (40 kV, 40 mA), 0-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ
Step size: 0.05° 2θ
Collection time: 0.5 s/step

Unless indicated otherwise, when calculating the peak positions from the XRPD-data, the data was first stripped from the contribution from CuKα2 and was then corrected against an internal standard (Al₂O₃).

The diffraction pattern of this novel crystal form of bis-choline tetrathiomolybdate was as set out in Table 3.

TABLE 3

XRPD Bis-choline tetrathiomolybdate Form 1

| Angle (°2-Theta) | Intensity (Count) | Intensity (%) |
|---|---|---|
| 10.60 | 250 | 10.6 |
| 11.14 | 174 | 7.4 |
| 11.30 | 236 | 10.0 |
| 12.64 | 1030 | 43.8 |
| 13.14 | 621 | 26.4 |
| 13.24 | 857 | 36.5 |
| 13.84 | 503 | 21.4 |
| 15.69 | 82 | 3.5 |
| 15.81 | 81 | 3.4 |
| 16.54 | 71 | 3.0 |
| 16.69 | 128 | 5.4 |
| 17.44 | 311 | 13.3 |
| 17.79 | 407 | 17.3 |
| 17.89 | 415 | 17.6 |
| 18.19 | 64 | 2.7 |
| 18.39 | 99 | 4.2 |
| 18.64 | 606 | 25.8 |
| 18.89 | 2350 | 100 |
| 19.86 | 421 | 17.9 |
| 20.54 | 68 | 2.9 |
| 20.14 | 124 | 5.3 |
| 20.64 | 75 | 3.2 |
| 21.04 | 50 | 2.1 |
| 21.29 | 181 | 7.7 |
| 21.55 | 95 | 4.0 |
| 21.79 | 192 | 8.2 |
| 21.94 | 160 | 6.8 |
| 22.43 | 137 | 5.8 |
| 22.69 | 84 | 3.6 |
| 23.01 | 40 | 1.7 |
| 23.29 | 296 | 12.6 |
| 23.39 | 310 | 13.2 |
| 23.48 | 386 | 16.4 |
| 23.74 | 264 | 11.2 |
| 24.28 | 236 | 10.1 |
| 24.74 | 73 | 3.1 |
| 25.04 | 318 | 13.5 |
| 25.28 | 55 | 2.3 |
| 25.44 | 146 | 6.2 |
| 25.74 | 59 | 2.5 |
| 25.94 | 67 | 2.8 |
| 26.33 | 102 | 4.3 |
| 26.44 | 57 | 2.4 |
| 26.69 | 151 | 6.4 |
| 26.83 | 57 | 2.4 |
| 27.23 | 57 | 2.4 |
| 27.59 | 53 | 2.3 |
| 28.29 | 380 | 16.2 |
| 28.53 | 91 | 3.9 |
| 28.88 | 91 | 3.9 |
| 29.48 | 280 | 11.9 |

Example 6. Bis-Choline Tetrathiomolybdate Form 2

Thermal analysis of bis-choline tetrathiomolybdate Form 1 showed the presence of a sharp endotherm at 56.8° C. Hot-Stage Microscopy showed that the endotherm did not relate to a melt but to a solid transition. Cycling differential scanning between room temperature to 80° C. showed that the transformation was reversible and the new bis-choline tetrathiomolybdate Form 2 found at temperature above the endotherm reverted to bis-choline tetrathiomolybdate Form 1 at room temperature.

Bis-choline tetrathiomolybdate Form 2 is thermally stable up to about 200° C. before degrading.

Bis-choline tetrathiomolybdate Form 1 was heated from room temperature to 60° C. at a rate of 10° C. per minute and the crystalline material was isolated.

XRPD analysis was performed as in Example 4. The X-ray powder diffraction pattern of this novel crystal form of bis-choline tetrathiomolybdate Form 2 is in Table 4.

TABLE 4

XRPD Bis-choline tetrathiomolybdate Form 2

| Angle (°2-Theta) | Intensity (Count) | Intensity (%) |
|---|---|---|
| 11.0 | 2526 | 36.1 |
| 12.84 | 7001 | 100 |
| 13.29 | 1958 | 28 |
| 16.02 | 1283 | 18.3 |
| 16.36 | 839 | 12 |
| 17.28 | 4079 | 58.3 |
| 17.89 | 830 | 11.8 |
| 19.08 | 4334 | 61.9 |
| 20.75 | 984 | 14.1 |
| 21.30 | 860 | 12.3 |
| 22.13 | 1440 | 20.6 |
| 22.85 | 2124 | 30.3 |
| 23.35 | 1786 | 25.5 |
| 25.09 | 665 | 9.5 |
| 25.87 | 1082 | 15.5 |
| 28.41 | 645 | 9.2 |
| 27.68 | 545 | 7.8 |
| 28.73 | 612 | 8.7 |
| 20.26 | 665 | 9.5 |
| 23.91 | 559 | 8 |
| 26.23 | 559 | 8 |
| 26.66 | 579 | 8.3 |

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

We claim:

1. A process for the production of compound (I):

comprising reacting compound (II):

with compound (III):

(III)

wherein
$X^{-1}$ is $OH^{-1}$, acetate, or a halide;
wherein the process comprises:
combining compound (II) with a first mixture of compound (III) in water, wherein a molar excess of compound (II) to compound (III) is used, for a first reaction period to provide a first reaction mixture;
subjecting the first reaction mixture to a reduced pressure for a second reaction period to provide a second reaction mixture; and,
isolating compound (I) from the second reaction mixture, wherein isolating compound (I) comprises adding ethanol to the second reaction mixture.

2. The process according to claim 1, wherein $X^{-1}$ is $OH^{-1}$.

3. The process according to claim 1, further comprising monitoring the evolution of ammonia during the step of subjecting the first reaction mixture to a reduced pressure.

4. The process according to claim 3, wherein monitoring the evolution of ammonia comprises measuring the pH of vapour of a gas phase in contact with the first reaction mixture.

5. The process according to claim 4, wherein achievement of pH of about 7 indicates that the second reaction period is complete.

6. The process according to claim 1, wherein isolating compound (I) comprises adding from 2 to 4 volumes of ethanol to the second reaction mixture, based on the total volume of the second reaction mixture.

7. The process according to claim 1, wherein the molar ratio of compound (II) to compound (III) is in the range of from 4 to 20.

8. The process according to claim 7, wherein the total reaction time of the process is reduced by at least 50% compared to a process in which compound (II) is not used in a molar excess.

9. The process according to claim 1, wherein less than about 25% w/w of compound (III) decomposes during the process.

10. The process according to claim 1, wherein the first mixture of compound (III) in water is a slurry of compound (III) in water.

11. The process according to claim 1, wherein the step of combining compound (II) with a first mixture of compound (III) in water is carried out at a temperature of 10° C. or less.

12. The process according to claim 1, wherein compound (II) is an aqueous solution.

13. The process according to claim 1, wherein the step of subjecting the first reaction mixture to a reduced pressure is carried out at a temperature of 35° C. or less.

14. The process according to claim 1, wherein the step of subjecting the first reaction mixture to a reduced pressure comprises subjecting the first reaction mixture to a pressure of 100 mbar or less.

15. The process according to claim 1, wherein the step of isolating compound (I) from the second reaction mixture comprises precipitating compound (I) from the second reaction mixture and optionally filtering the second reaction mixture to obtain compound (I) as a solid.

16. The process according to claim 1, further comprising a recrystallization step, followed by optional polish filtering, optional washing with ethanol, drying of the resultant solid, and measurement of resulting particle size of the resultant solid.

17. The process according to claim 16, wherein the resultant solid has a 50th percentile of particle size ($D_{50}$) of at least 30 μm.

18. The process according to claim 16, wherein the resultant solid has a 90th percentile of particle size ($D_{90}$) of between 60 μm and 550 μm.

19. The process according to claim 16, wherein the resultant solid has a $D_{50}$ of less than 35 μm, a $D_{90}$ of less than 75 μm, or both.

20. The process according to claim 16, wherein the resultant solid has a $D_{90}$-to-$D_{50}$ ratio of less than 3.0.

* * * * *